United States Patent [19]

Parker et al.

[11] Patent Number: 4,541,901

[45] Date of Patent: Sep. 17, 1985

[54] METHOD AND APPARATUS FOR ZERO CALIBRATION OF OXYGEN-SENSING POLAROGRAPHIC DEVICES

[75] Inventors: Dawood Parker; David T. Delpy, both of London, England

[73] Assignee: Novametrix Medical Systems, Inc., Wallingford, Conn.

[21] Appl. No.: 603,718

[22] Filed: Apr. 25, 1984

[30] Foreign Application Priority Data

Apr. 27, 1983 [GB] United Kingdom ............... 8311541

[51] Int. Cl.$^4$ ........................... G01N 27/46
[52] U.S. Cl. ................... 204/1 T; 204/402; 204/415
[58] Field of Search ........... 204/1 T, 1 P, 402, 401, 204/400, 415

[56] References Cited

U.S. PATENT DOCUMENTS

| | | | |
|---|---|---|---|
| 2,805,191 | 9/1957 | Hersch | 204/402 |
| 3,088,905 | 5/1963 | Glover | 204/415 |
| 3,328,277 | 6/1967 | Solomons et al. | 204/415 |
| 3,454,485 | 7/1969 | Hauk et al. | 204/1 P |
| 3,526,577 | 9/1970 | Molloy | 204/415 |
| 4,092,233 | 5/1978 | Clemens et al. | 204/415 |
| 4,170,523 | 10/1979 | Buzza et al. | 204/401 |

Primary Examiner—T. Tung
Attorney, Agent, or Firm—Howard F. Mandelbaum

[57] ABSTRACT

The calibration of a polarographic oxygen sensor (20) at zero oxygen concentration is accomplished by providing an oxygen-free liquid environment at the sensor active surface. This is accomplished electrolytically by depleting a thin film of electrolyte (24) of oxygen to zero concentration with an oxygen-reducing cathode (6), and complementary anode (4), connected via a battery (10) and switch (12). The sensor (20) is placed into close proximity with the electrodes (4,6) and the oxygen in the electrolyte (24) reduced while its concentration is measured by the sensor (20). A low steady-state signal for the sensor provides the zero oxygen concentration calibration point.

7 Claims, 1 Drawing Figure

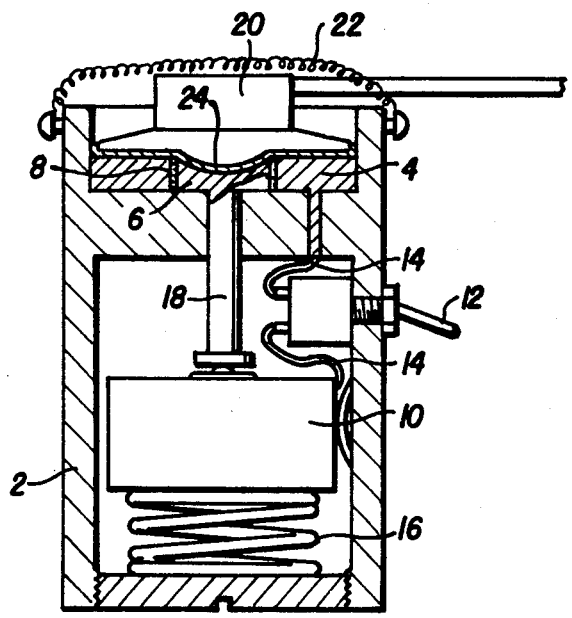

METHOD AND APPARATUS FOR ZERO CALIBRATION OF OXYGEN-SENSING POLAROGRAPHIC DEVICES

This invention relates to a method and apparatus for the zero calibration of polarographic oxygen sensors such as polarographic transcutaneous oxygen sensors.

Such oxygen-sensing devices are usually calibrated at two oxygen concentrations. Zero oxygen concentration is used as one calibration point and the other point is normally taken as the oxygen concentration in atmospheric air. The latter calibration can be easily accomplished by merely holding the sensor in air and requires no extra equipment. However, the zero calibration requires a more complex procedure.

At present, zero calibration is usually accomplished by one of two methods. However, both these methods have certain inherent disadvantages.

The first method involves the use of a cylinder or supply of an oxygen-free gas, such as nitrogen. However, this requirement of access to a suitable gas supply or cylinder has proven disadvantageous since it tends to limit the number of locations in which this technique of calibration can be used, and such supplies are bulky.

The second method involves placing a drop of an oxygen-free solution on to the face of the sensor, such as a mixture of sodium sulphite and borax in solution. However, this technique has two main disadvantages.

Firstly the sodium sulphite/borax solution has a limited lifetime once it has been prepared. Secondly, the solution must not be left in contact with the sensor membrane for more than two to three minutes since, if it penetrates the membrane through any small flaw and enters the inner electrolyte of the sensor, the sulphite will be reduced at the cathode and an error current will be produced.

The present invention is concerned with obviating these problems by providing a method and apparatus for zero calibrating oxygen-sensing polarographic devices which is simple, reliable, portable and suitable for routine use.

The present invention utilises the fact that oxygen present in an electrolyte may be consumed by electrolytic-reduction at a suitable cathode. If it can be arranged that the rate of reduction is faster than the dissolution of oxygen into the electrolyte, then the latter becomes depleted of oxygen and eventually oxygen-free. Such an electrolyte may then be employed for the zero point calibration of the oxygen sensors as described.

According to a first aspect of the present invention there is provided an apparatus for calibrating a polarographic oxygen sensor at substantially zero concentration of oxygen, which comprises a pair of electrodes which, in use with a suitable electrolyte in contact therewith, act respectively as a cathode for the reduction of oxygen in the electrolyte and as a complementary anode, means for electrically connecting said electrodes, and means to enable a polarographic oxygen sensor to be disposed closely adjacent said electrodes whereby, in use, oxygen is depleted by electrolytic reduction from said electrolyte to substantially zero concentration and said sensor monitors said concentration.

According to a second aspect of the invention there is provided a method of calibrating a polarographic oxygen sensor at substantially zero concentration of oxygen, which comprises disposing the sensor in an electrolyte closely adjacent a pair of electrodes which act respectively as a cathode for the reduction of oxygen in the electrolyte and as a complementary anode, electrically-connecting said electrodes and arranging for the oxygen to be depleted from said electrolyte by electrolytic reduction to substantially zero concentration, and monitoring the oxygen concentration with said sensor at substantially zero.

The electrical energy necessary to reduce the oxygen in the electrolyte may be provided by supplying an external energy source, such as a battery. Alternatively it may be derived from the electrodes themselves if they are of a combination, in relation to the electrolyte, such as provides a galvanic couple and automatically reduces oxygen when electrically-connected.

The apparatus may be a self-contained unit or it may be installed integrally with the electrical control and monitoring apparatus for the oxygen sensor. In the latter event, the power source for the oxygen sensor may also be employed to drive the calibration apparatus.

In order to achieve oxygen depletion to zero concentration in an acceptable time, it is desirable that the oxygen consuming cathode should be as large as possible, and the volume of electrolyte to be depleted should be minimised. This may be achieved by arranging that the electrodes have a profile adjacent the abutting face of the oxygen sensor such that only a thin layer of electrolyte lies therebetween. It is desirable that the anode has a sufficient surface area to avoid polarisation effects at the operating current density. A small anode current will cause the reduction current to be anode-limited, and hence increase the response time.

Numerous materials may be employed for the electrolyte and for the electrode materials. The electrolyte should have a high electrical conductivity so that the reduction current is not limited by the current density of the liquid. Several electrolytes containing halide ions (above impurity levels), particularly chloride ions, are suitable. A convenient electrolyte, especially for physiological oxygen sensors, is physiological saline of high chloride concentration (e.g. 0.5M or higher).

The electrodes are typically of noble metals (e.g. platinum, silver), the combination being selected such that the selected cathode is capable of reducing oxygen in relation to the selected anode. High purity for the electrodes is not essential.

The reducing voltage applied between the electrodes should be as high as conveniently possible so to maximise the reduction reaction efficiency and hence minimise the response time. Typically a voltage of about 1 volt is sufficient.

The oxygen sensor may fit snugly against and above the reducing cathode, with a thin film of electrolyte (or an "O" ring) to act as a seal preventing oxygen diffusing into the system. This may be achieved by placing excess electrolyte onto the electrodes and disposing the sensor thereabove, adjacent the electrodes. The excess electrolyte is squeezed out to form the desired seal and a thin film of electrolyte between the cathode and sensor. Any air bubbles are also thus flushed from the system.

A preferred calibration apparatus in accordance with the invention will now be described with reference to the accompanying drawing, given by way of example; the drawing being a schematic vertical cross-section through the apparatus in use for calibration of a physiological polarographic transcutaneous oxygen sensor.

Referring to the drawing, a cylindrical casing 2 supports an annular silver anode 4 surrounding a central silver cathode 6. Anode 4 and cathode 6 are separated by an electrically-insulating ring 8. Electrical connection between the anode and cathode is effected through a 1.0–1.1 volt secondary battery 10, switch 12 and connectors 14. A spring 16 biasses the battery against a downwardly-extending stem 18 of the cathode 6.

A physiological polarographic oxygen sensor 20 which is to be zero-calibrated abuts the anode and cathode, and is biassed thereagainst by spring clip 22. The anode and cathode faces adjacent the sensor 20 are profiled to provide a complementary surface thereto. A small quantity of physiological saline 24 (0.5M or higher in concentration) is disposed between the sensor 20 and anode 4, cathode 6.

In use, the sensor 20 having been assembled in the calibration apparatus as described and switched on, the switch 12 is switched to "on" and the electrical current which passes causes any oxygen in the saline to be reduced at the cathode. The amount of saline is so small, and the apparatus so constructed that the reduction rapidly depletes the solution of oxygen until it effectively reaches zero concentration. During this time the output from sensor 20 is monitored and shows a decreasing signal representative of the loss of oxygen from the saline. When the sensor signal reaches a steady state low signal, the latter is taken as the zero calibration for the sensor.

We claim:

1. An apparatus comprising a polarographic oxygen sensor with sensing electrodes disposed on one side of an oxygen permeable barrier, which has a sensing surface of predetermined contour on an opposite side of said barrier, a pair of electrodes acting respectively as a cathode and as an anode, insulating means between said cathode and anode, at least one of said cathode, anode and insulating means having a complementary surface with a contour which is in complementary conformity with the contour of said sensing surface, an electrolyte layer bridging the space between said complementary surface and said sensing surface and contacting said pair of electrodes, means for electrically connecting said pair of electrodes to complete an electic circuit through said electrolyte, and means removably mounting said polarographic oxygen sensor with said sensing surface in closely spaced relationship to said complementary surface whereby, in use, oxygen is depleted by electrolytic reduction from said layer of electrolyte to substantially zero concentration whereby said sensor can monitor said zero concentration during calibration thereof.

2. An apparatus according to claim 1, wherein a source of electrical energy is included in said electrically connecting means.

3. An apparatus according to claim 1, wherein said pair of electrodes when electrically-connected form a galvanic cell in use in the electrolyte.

4. An apparatus according to claim 1, wherein said electodes are concentrically-disposed.

5. A method of calibrating a polarographic oxygen sensor with sensing electrodes disposed on one side of an oxygen permeable barrier, which has a sensing surface of predetermined contour on an opposite side of said barrier, at substantially zero concentration of oxygen, comprising mounting said sensor in closely spaced relationship to a surface with a contour which is in complementary conformity with the contour of said sensing surface and upon which there is a layer of an electrolyte applying a voltage across an anode and a cathode in contact with said electrolyte at a sufficient magnitude to cause reduction of the oxygen therein at a rate greater than the absorbtion of ambient oxygen into said electrolyte, and scaling an oxygen measurement apparatus responsive to the output of said sensor to indicate zero concentration and dismounting said sensor from its position adjacent the surface carrying the layer of electrolyte.

6. A method according to claim 5 wherein said voltage is applied by an electrical source connected to said pair of electrodes.

7. A method according to claim 5, wherein said voltage is applied by the galvanic action of the pair of electrodes.

* * * * *